United States Patent
Bhatt et al.

(10) Patent No.: US 10,653,656 B2
(45) Date of Patent: May 19, 2020

(54) TOPICAL PHARMACEUTICAL COMPOSITIONS FOR TREATING SKIN CONDITIONS

(71) Applicant: BAUSCH HEALTH IRELAND LIMITED, Dublin (IE)

(72) Inventors: Varsha Bhatt, San Francisco, CA (US); Radhakrishnan Pillai, Santa Rosa, CA (US)

(73) Assignee: Bausch Health Ireland Limited, Dublin (IE)

( * ) Notice: Subject to any disclaimer, the term of this patent is extended or adjusted under 35 U.S.C. 154(b) by 0 days.

(21) Appl. No.: 16/108,942

(22) Filed: Aug. 22, 2018

(65) Prior Publication Data

US 2019/0307716 A1    Oct. 10, 2019

Related U.S. Application Data

(60) Provisional application No. 62/653,392, filed on Apr. 5, 2018.

(51) Int. Cl.
| | | |
|---|---|---|
| *A61K 31/203* | (2006.01) | |
| *A61K 9/06* | (2006.01) | |
| *A61K 47/32* | (2006.01) | |
| *A61K 47/44* | (2017.01) | |
| *A61P 17/10* | (2006.01) | |
| *A61K 47/14* | (2017.01) | |
| *A61K 47/10* | (2017.01) | |
| *A61K 47/18* | (2017.01) | |
| *A61K 47/36* | (2006.01) | |

(52) U.S. Cl.
CPC .............. *A61K 31/203* (2013.01); *A61K 9/06* (2013.01); *A61K 47/10* (2013.01); *A61K 47/14* (2013.01); *A61K 47/18* (2013.01); *A61K 47/32* (2013.01); *A61K 47/36* (2013.01); *A61K 47/44* (2013.01); *A61P 17/10* (2018.01)

(58) Field of Classification Search
None
See application file for complete search history.

(56) References Cited

U.S. PATENT DOCUMENTS

| | | | |
|---|---|---|---|
| 5,670,547 A * | 9/1997 | Milstein ............ | A61K 8/64 514/725 |
| 6,387,383 B1 | 5/2002 | Dow et al. | |
| 6,517,847 B2 | 2/2003 | Dow et al. | |
| 6,531,141 B1 | 3/2003 | Marvel | |
| 6,709,663 B2 | 3/2004 | Espinoza | |
| 7,300,669 B2 | 11/2007 | Dow et al. | |
| 7,368,122 B1 | 5/2008 | Dow et al. | |
| 8,809,307 B2 | 8/2014 | Angel et al. | |
| 2014/0274982 A1 | 9/2014 | Bakan et al. | |
| 2016/0367570 A1 | 12/2016 | Dow et al. | |
| 2018/0243420 A1 | 8/2018 | Angel et al. | |

FOREIGN PATENT DOCUMENTS

EP    0 421 333 A1    4/1991

OTHER PUBLICATIONS

Brisaert et al, "Investigation on the photostability of a tretinoin lotion and stabilization with additives," International Journal of Pharmaceutics, vol. 199, No. 1, pp. 49-57 (Year: 2000).*
Khalil, S. et al., "Retinoids: a journey from the molecular structures and mechanisms of action to clinical uses in dermatology and adverse effects." Journal of Dermatological Treatment, Mar. 2017, 28:8, 684-696.
Kircik, LH, "Evaluating tretinoin formulations in the treatment of acne," J. Drugs Dermatol, 2014, 13(4):466-470.
Lubrizol Technical Data Sheet, "Skin Care Products Formulated with Pemulen® Polymeric Emulsifiers" Oct. 15, 2007, The Lubrizol Corporation.
International Search Report issued in connection with corresponding International Application No. PCT/US2019/026016, dated Jun. 21, 2019, 2 pages.
Bergfeld et al. "Crosslinked Alkyl Acrylates as Used in Cosmetics." Cosmetic Ingredient Review, Nov. 17, 2011, 7 pages, http://www.cir.safety.org/sites/default/files/cross1092011final_for%20posting.pdf.
Draganoiu et al. "Properties of Mucoadhesive Polymers and Their Use in Tablets and Other Dosage Forms." www.tabletscapsules.com, CSC Publishing, Jul. 1, 2016, 7 paegs, www.pharmaexcipients.com/wp-content/uploads/attachments/tc_20160701_0017.pdf?t=1471335016.
Tegeli et al. "Pemulen as a Versatile Emulsifier." International Journal of Drug Formulation and Research, vol. 2, No. 1, 2011, 4 pages, https://www.academia.edu/760778/PEMULEN AS A_VERSATILE_EMULSIFIER.
Lubrizol. "Toxicity of Carbopol Polymers As a Class." Lubrizol Advanced Materials, Inc., May 31, 2011, 2 pages.
"Mineral Oil." Drug Bank, Dec. 3, 2015, 7 pages. www.drugbank.ca/drugs/DB11057.
Coria Laboratories, Ltd. "Highlights of Prescribing Information." Coria Laboratories, Ltd, Jul. 2007, 9 pages.

* cited by examiner

*Primary Examiner* — Dennis J Parad
(74) *Attorney, Agent, or Firm* — Kilpatrick Townsend & Stockton LLP

(57) ABSTRACT

In one aspect, topical pharmaceutical compositions for treating a skin condition or disorder are provided. In some embodiments, the topical pharmaceutical composition is formulated as a lotion and comprises a therapeutically effective amount of an active agent; a viscosity increasing agent; a polymeric emulsifier; and an oil component. In some embodiments, the topical pharmaceutical composition comprises tretinoin.

21 Claims, No Drawings

000
TOPICAL PHARMACEUTICAL COMPOSITIONS FOR TREATING SKIN CONDITIONS

CROSS-REFERENCE TO RELATED APPLICATIONS

This application claims priority to U.S. Provisional Patent Application No. 62/653,392, filed Apr. 5, 2018, the entire contents of which are incorporated by reference herein.

BACKGROUND OF THE INVENTION

Skin disorders such as acne, dermatitis, and rosacea are common conditions for juveniles and adults. A number of different agents, including retinoids, corticosteroids, antibiotics, and anti-inflammatory agents, are prescribed for the treatment of skin disorders. For example, retinoids such as tretinoin are commonly prescribed for the treatment of acne and for reducing or improving fine wrinkling, dark spots, and rough facial skin. However, a known side effect of retinoids is irritation at the site of local application, such as burning, dry skin, erythema and exfoliation. Likewise, the antibiotic clindamycin, which is prescribed for the treatment of acne, is associated with side effects such as burning or itching skin, dry skin, skin redness, and skin peeling. There remains a need for topical compositions that have reduced adverse effects for the treatment of acne and other skin conditions.

BRIEF SUMMARY OF THE INVENTION

In one aspect, topical pharmaceutical compositions for treating a skin condition or disorder are provided. In some embodiments, a topical pharmaceutical composition comprises:
  a therapeutically effective amount of an active agent that is useful for treating the skin condition or disorder;
  a viscosity increasing agent;
  a polymeric emulsifier, wherein the polymeric emulsifier is present in an amount up to about 0.2% by weight of the composition; and
  an oil component;
  wherein the composition is formulated as a lotion.

In some embodiments, the active agent is a retinoid, a corticosteroid, an antibiotic, or an anti-inflammatory agent. In some embodiments, the active agent is a retinoid. In some embodiments, the retinoid is tretinoin. In some embodiments, the active agent (e.g., a retinoid, a corticosteroid, an antibiotic, or an anti-inflammatory agent) is present in an amount from about 0.001% to about 1% by weight of the composition. In some embodiments, the active agent (e.g., a retinoid, a corticosteroid, an antibiotic, or an anti-inflammatory agent) is present in an amount of about 0.05% by weight of the composition.

In some embodiments, the polymeric emulsifier comprises a cross-linked copolymer of acrylic acid and C10-C30 alkyl acrylate. In some embodiments, the polymeric emulsifier is present in an amount from about 0.01% to about 0.2% by weight of the composition. In some embodiments, the polymeric emulsifier is present in an amount from about 0.01% to about 0.1% by weight of the composition. In some embodiments, the polymeric emulsifier is present in an amount of about 0.05% by weight of the composition.

In some embodiments, the oil component comprises mineral oil. In some embodiments, the oil component (e.g., mineral oil) is present in an amount up to about 20% by weight of the composition. In some embodiments, the oil component (e.g., mineral oil) is present in an amount up to about 10% by weight of the composition. In some embodiments, the oil component (e.g., mineral oil) is present in an amount up to about 5% by weight of the composition. In some embodiments, the oil component (e.g., mineral oil) is present in an amount from about 1% to about 5% by weight of the composition. In some embodiments, the oil component (e.g., mineral oil) is present in an amount from about 2% to about 10% by weight of the composition. In some embodiments, the oil component (e.g., mineral oil) is present in an amount from about 2% to about 4% by weight of the composition. In some embodiments, the oil component (e.g., mineral oil) is present in an amount of about 2% by weight of the composition.

In some embodiments, the viscosity increasing agent comprises a cross-linked homopolymer of an acrylic acid. In some embodiments, the viscosity increasing agent is present in an amount from about 0.1% to about 2% by weight of the composition. In some embodiments, the viscosity increasing agent is present in an amount from about 0.2% to about 1% by weight of the composition. In some embodiments, the viscosity increasing agent is present in an amount from about 0.4% to about 1% by weight of the composition. In some embodiments, the viscosity increasing agent is present in an amount from about 0.6% to about 1% by weight of the composition.

In some embodiments, the topical pharmaceutical composition further comprises one or more additional components. In some embodiments, the topical pharmaceutical composition further comprises one or more preservatives, one or more moisturizing agents, one or more antioxidants, and/or one or more humectants. In some embodiments, the topical pharmaceutical composition further comprises a neutralizing agent that maintains the pH of the composition at a pH from about 5 to about 7. In some embodiments, the topical pharmaceutical composition further comprises a neutralizing agent that maintains the pH of the composition at a pH from about 5 to about 6.

In some embodiments, the topical pharmaceutical composition comprises:
  tretinoin in an amount from about 0.001% to about 1% by weight of the composition;
  a viscosity increasing agent in an amount from about 0.6% to about 1% by weight of the composition;
  a polymeric emulsifier in an amount from about 0.04% to about 0.06% by weight of the composition;
  mineral oil in an amount from about 1% to about 5% by weight of the composition;
  one or more humectants, moisturizing agents, antioxidants, preservatives, wetting agents, and/or neutralizing agents; and
  water.

In some embodiments, the topical pharmaceutical composition has a viscosity from about 2,500 cP to about 18,000 cP. In some embodiments, the topical pharmaceutical composition has a viscosity from about 8,000 cP to about 12,000 cP. In some embodiments, the topical pharmaceutical composition has a viscosity of less than about 15,000 cP. In some embodiments, the topical pharmaceutical composition has a viscosity of at least about 2,500 cP.

In some embodiments, the topical pharmaceutical composition is formulated as a lotion and comprises:
  tretinoin in an amount from about 0.01% to about 1% by weight of the composition;
  a polymeric emulsifier, wherein the polymeric emulsifier comprises a cross-linked copolymer of acrylic acid and C10-C30 alkyl acrylate and wherein the polymeric emulsifier is present in an amount from to about 0.01% to about 0.2% by weight of the composition;

a viscosity increasing agent, wherein the viscosity increasing agent comprises a cross-linked homopolymer of an acrylic acid; and an oil component.

In some embodiments, the topical pharmaceutical composition comprises tretinoin in an amount of about 0.05% by weight of the composition. In some embodiments, the polymeric emulsifier is a carbomer copolymer type B. In some embodiments, the polymeric emulsifier is present in an amount from about 0.04% to about 0.06% by weight of the composition. In some embodiments, the oil component comprises mineral oil. In some embodiments, the oil component is present in an amount up to about 5% by weight of the composition, e.g., in an amount from about 2% to about 4% by weight of the composition. In some embodiments, the viscosity increasing agent is a carbomer homopolymer type A. In some embodiments, the viscosity increasing agent is present in an amount from about 0.1% to about 2% by weight of the composition. In some embodiments, the viscosity increasing agent is present in an amount from about 0.6% to about 1% by weight of the composition. In some embodiments, the topical pharmaceutical composition further comprises one or more preservatives, moisturizing agents, antioxidants, and/or humectants. In some embodiments, the topical pharmaceutical composition further comprises a neutralizing agent that maintains the pH of the composition at a pH from about 5 to about 6.

In some embodiments, a topical pharmaceutical composition for treating a skin condition or disorder is formulated as a lotion and comprises:

tretinoin an amount of about 0.05% by weight of the composition;

a carbomer copolymer type B in an amount from about 0.04% to about 0.06% by weight of the composition;

a carbomer homopolymer type A in an amount from about 0.2% to about 1% by weight of the composition;

mineral oil in an amount from about 2% to about 4% by weight of the composition;

one or more preservatives, moisturizing agents, antioxidants, humectants, wetting agents, and/or neutralizing agents; and water.

In some embodiments, the topical pharmaceutical composition comprises one or more moisturizing agents in an amount from about 5% to about 20% by weight of the composition, wherein the moisturizing agents are sodium hyaluronate, soluble collagen, or a combination thereof; a humectant in an amount from about 5% to about 20% by weight of the composition, wherein the humectant is glycerin; an antioxidant in an amount from about 0.1% to about 2% by weight of the composition, wherein the antioxidant is butylated hydroxytoluene; a wetting agent in an amount from about 0.05% to about 0.5% by weight of the composition, wherein the wetting agent is octoxynol-9; optionally, one or more preservatives in an amount from about 0.25% to about 5% by weight of the composition, wherein the preservatives are benzyl alcohol, methyl paraben, or a combination thereof; and optionally, a neutralizing agent, wherein the neutralizing agent is trolamine.

In another aspect, kits are provided. In some embodiments, the kit comprises a topical pharmaceutical composition as disclosed herein. In some embodiments, the kit further comprises instructions for use, e.g., according to a method as disclosed herein. In some embodiments, the kit is for use in treating a skin condition or disorder as disclosed herein, e.g., acne vulgaris.

In yet another aspect, methods for treating a skin condition or disorder are provided. In some embodiments, the method comprises administering a topical pharmaceutical composition as disclosed herein to a subject in need thereof. In some embodiments, the skin condition or disorder is acne vulgaris. In some embodiments, the topical pharmaceutical composition is applied once daily to an affected area of skin.

DETAILED DESCRIPTION OF THE INVENTION

I. Introduction

Disclosed herein are pharmaceutical compositions, kits, and methods for the treatment of acne and other skin conditions or disorders. As disclosed herein, it has been surprisingly found that an active agent, tretinoin, could be formulated as a lotion with a low concentration of a polymeric emulsifier and a low concentration of mineral oil, and that the resulting lotion had a light, elegant feel. It was also surprisingly found that the resulting lotion exhibited a marked improvement in the tolerability profile of the tretinoin composition, as compared to the tolerability profile of commercially available tretinoin having the same amount of active ingredient but formulated as a gel. Thus, in one aspect, the topical pharmaceutical compositions disclosed herein provide unexpectedly improved properties, as compared to commercially available products, when used in the treatment of skin conditions.

II. Definitions

As used herein, the singular forms "a," "an," and "the" include plural referents unless the content clearly dictates otherwise. The terms "about" and "approximately," when used to modify an amount specified in a numeric value or range, indicate that the numeric value as well as reasonable deviations from the value known to the skilled person in the art, for example, ±20%, ±10%, or ±5%, are within the intended meaning of the recited value.

The terms "subject," "individual," and "patient," as used interchangeably herein, refer to a mammal, including but not limited to humans, non-human primates, rodents (e.g., rats, mice, and guinea pigs), rabbits, dogs, cows, pigs, horses, and other mammalian species. In some embodiment, a subject, individual, or patient is a human.

As used herein, the terms "treat" and "treatment" refer to any indicia of success in the treatment or amelioration of an injury, disease, or condition (e.g., acne or another skin condition), including any objective or subjective parameter such as abatement, remission, improvement in patient survival, increase in survival time or rate, diminishing of symptoms or making the injury, disease, or condition more tolerable to the patient, slowing in the rate of degeneration or decline, or improving a patient's physical or mental well-being. The effect of treatment can be compared to an individual or pool of individuals not receiving the treatment, or to the same patient prior to treatment or at a different time during treatment.

As used herein, the term "therapeutically effective amount" refers to an amount of an agent (e.g., a retinoid) that treats, alleviates, abates, or reduces the severity of symptoms of disease in a subject. In some embodiments, a therapeutically effective amount of an agent (e.g., a retinoid) diminishes symptoms, makes an injury, disease, or condition (e.g., a skin disorder) more tolerable, slows the rate of degeneration or decline, improves patient survival, increases survival time or rate, or improves a patient's physical or mental well-being.

As used herein, the term "administer" refers to a method of delivering agents, compounds, or compositions to the desired site of biological action. These methods include, but are not limited to, topical delivery, parenteral delivery, intravenous delivery, intradermal delivery, intramuscular delivery, colonic delivery, rectal delivery, or intraperitoneal delivery. In some embodiments, a composition as disclosed herein is administered topically.

III. Topical Pharmaceutical Compositions

In one aspect, topical pharmaceutical compositions for the treatment of a skin condition or disorder are provided. In some embodiments, the pharmaceutical composition comprises: a therapeutically effective amount of an active agent that is useful for treating the skin condition or disorder (such as, but not limited to, a retinoid, a corticosteroid, an antibiotic, or an anti-inflammatory agent); a viscosity increasing agent; a polymeric emulsifier; and an oil component. In some embodiments, the composition is formulated as a lotion.

In some embodiments, the pharmaceutical composition has a viscosity from about 2,500 cP to about 18,000 cP. In some embodiments, the topical pharmaceutical composition has a viscosity of less than about 15,000 cP. In some embodiments, the pharmaceutical composition has a viscosity from about 8,000 cP to about 12,000 cP, e.g., a viscosity from about 9,000 cP to about 11,000 cP. In some embodiments, viscosity is measured at 22-25° C., using a viscometer, e.g., a Brookfield rotational viscometer using spindle 27 and a speed of 12 rpm.

Active Agents

In some embodiments, the topical pharmaceutical compositions of the present disclosure comprise one or more active agents that are known to be useful for treating a skin condition or disorder. In some embodiments, the pharmaceutical composition comprises an active agent selected from the group consisting of a retinoid, a corticosteroid, an antibiotic, and an anti-inflammatory agent.

In some embodiments, the topical pharmaceutical composition comprises a retinoid. The term "retinoid," as used herein, refers to a compound that is a retinol (Vitamin A) or an analog or derivative thereof. A retinoid may be naturally occurring or synthetic. Examples of retinoids include, but are not limited to, retinol, retinal, tretinoin, isotretinoin, alitretinoin, etretinate, acitretin, adapalene, bexarotene, and tazarotene. In some embodiments, the retinoid is in the form of a pharmaceutically acceptable salt, ester, isomer, enantiomer, active metabolite, or prodrug. Retinoids are described in the art. See, e.g., Khalil et al., *Journal of Dermatological Treatment,* 2017, 28:684-696.

In some embodiments, the topical pharmaceutical composition comprises tretinoin. The term "tretinoin," as used herein, refers to all-trans-retinoic acid, also known in the art as (all-E)-3,7-dimethyl-9-(2,6,6-trimethyl-1-cyclohexen-1-yl)-2,4,6,8-nonatetraenoic acid. Tretinoin has the following chemical structure:

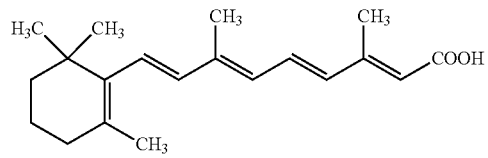 [SMILES: CC1=C(/C=C/C(C)=C/C=C/C(C)=C/C(=O)O)C(C)(C)CCC1]

In some embodiments, the topical pharmaceutical composition comprises a retinoid or a pharmaceutically acceptable salt thereof. In some embodiments, the pharmaceutical composition comprises a first-generation retinoid, e.g., retinol, retinal, tretinoin, isotretinoin, or alitretinoin. In some embodiments, the pharmaceutical composition comprises a second-generation retinoid, e.g., etretinate or its metabolite acetretin. In some embodiments, the pharmaceutical composition comprises a third-generation retinoid, e.g., adapalene, bexarotene, or tazarotene.

In some embodiments, the topical pharmaceutical composition comprises a corticosteroid. The term "corticosteroid," as used herein, refers to a steroid hormone that is produced by the adrenal cortex or a synthetic analog or derivative thereof. Corticosteroids are categorized into seven classes according to their potency as determined based on their vasoconstrictive activity (e.g., as measured in a VasoConstrictor Assay (VCA). The VCA test is known in the art. See, e.g., U.S. Pat. No. 7,300,669. In some embodiments, the corticosteroid is a Class 1 corticosteroid ("Superpotent Corticosteroid"), a Class 2 corticosteroid ("Potent Corticosteroid"), or a Class 3 corticosteroid ("Upper Mid-Strength Corticosteroid"). In some embodiments, the corticosteroid is clobetasol, halobetasol, betamethasone, fluocinonide, diflorasone, desoximetasone, mometasone, flurandrenolide, halcinonide, amcinonide, budesonide, desonide, beclomethasone, triamcinolone, fluticasone, hydrocortisone, or fluocinolone. In some embodiments, the corticosteroid is selected from the group consisting of clobetasol propionate, halobetabol propionate, betamethasone dipropionate, betamethasone valerate, fluocinonide, diflorasone diacetate, desoximetasone, mometasone furoate, flurandrenolide, halcinonide, amcinonide, budesonide, desonide, beclomethasone, fluticasone propionate, hydrocortisone butyrate, hydrocortisone valerate, fluocinolone acetonide, and triamcinolone acetonide.

In some embodiments, the topical pharmaceutical composition comprises an antibiotic. As used herein, an "antibiotic" is an agent that inhibits the growth of an unwanted microorganism. Examples of antibiotics include, but are not limited to, clindamycin, erythromycin, natamycin, neomycin, mupirocin, fusidic acid, minocycline, dapsone, and tetracycline, or a pharmaceutically acceptable salt, ester, or prodrug thereof. In some embodiments, the pharmaceutical composition is clindamycin, e.g., clindamycin phosphate.

In some embodiments, the topical pharmaceutical composition comprises an anti-inflammatory agent. As used herein, an "anti-inflammatory agent" is a compound that suppresses a topical inflammatory response. In some embodiments, the anti-inflammatory agent is an imidazole compound that suppresses a topical inflammatory response, such as but not limited to metronidazole. In some embodiments, the anti-inflammatory agent is a nonsteroidal anti-inflammatory agent (NSAID) that suppresses the inflammatory response when topically applied by inhibiting prostaglandin synthesis or by other mechanisms of action.

Examples of topical NSAIDs include, but are not limited to, ibuprofen, indomethacin, diclofenac, and naproxen and their salts.

In some embodiments, the topical pharmaceutical composition comprises an active agent (e.g., a corticosteroid, an antibiotic, an anti-inflammatory agent, or a retinoid, e.g., tretinoin) in a therapeutically effective amount. In some embodiments, the pharmaceutical composition comprises an active agent (e.g., a corticosteroid, an antibiotic, an anti-inflammatory agent, or a retinoid, e.g., tretinoin) in an amount from about 0.001% to about 1% by weight of the composition, e.g., in an amount from about 0.01% to about 1%, from about 0.01% to about 0.5%, from about 0.01% to about 0.1%, from about 0.01% to about 0.06%, from about 0.02% to about 0.06%, from about 0.01% to about 0.05%, from about 0.05% to about 1%, from about 0.05% to about 0.5%, from about 0.05% to about 0.1%, from about 0.1% to about 1%, from about 0.1% to about 0.75%, or from about 0.1% to about 0.5% by weight of the composition. In some embodiments, the pharmaceutical composition comprises an active agent (e.g., a corticosteroid, an antibiotic, an anti-inflammatory agent, or a retinoid, e.g., tretinoin) in an amount up to about 1% by weight of the composition, e.g., up to about 0.75% or up to about 0.5%, or up to about 0.1%, or up to about 0.06%, or up to about 0.05% by weight of the composition. In some embodiments, the pharmaceutical composition comprises a retinoid (e.g., tretinoin) in an amount that is less than about 1% by weight of the composition, e.g., less than 0.75%, or less than 0.5%, or less than 0.1%, or less than 0.06%, or less than 0.05% by weight of the composition. In some embodiments, the pharmaceutical composition comprises an active agent (e.g., a corticosteroid, an antibiotic, an anti-inflammatory agent, or a retinoid, e.g., tretinoin) in an amount of about 0.001%, about 0.005%, about 0.01%, about 0.05%, about 0.1%, about 0.2%, about 0.3%, about 0.4%, about 0.5%, about 0.6%, about 0.7%, about 0.75%, about 0.8%, about 0.9%, or about 1% by weight of the composition.

In some embodiments, the topical pharmaceutical composition comprises tretinoin as the active agent. In some embodiments, the tretinoin is present in an amount from about 0.001% to about 1% by weight of the composition, e.g., in an amount of 0.05% by weight of the composition.

In some embodiments, the active agent (e.g., a corticosteroid, an antibiotic, an anti-inflammatory agent, or a retinoid, e.g., tretinoin) is suspended in the composition. In some embodiments, the active agent (e.g., a corticosteroid, an antibiotic, an anti-inflammatory agent, or a retinoid, e.g., tretinoin) is solubilized (e.g., partially solubilized or fully solubilized) in the composition.

In some embodiments, the topical pharmaceutical composition comprises two or more active agents. For example, in some embodiments, the pharmaceutical composition comprises a retinoid (e.g., tretinoin) and an antimicrobial or an antibiotic (e.g., clindamycin). In some embodiments, wherein the pharmaceutical composition comprises two or more active agents, each active agent is present in an amount from about 0.001% to about 1% by weight of the composition, e.g., from about 0.01% to about 1%, from about 0.01% to about 0.5%, from about 0.01% to about 0.1%, from about 0.01% to about 0.06%, from about 0.01% to about 0.1%, from about 0.01% to about 0.05%, from about 0.05% to about 1%, from about 0.05% to about 0.5%, from about 0.05% to about 0.1%, from about 0.1% to about 1%, from about 0.1% to about 0.75%, or from about 0.1% to about 0.5% by weight of the composition.

Viscosity Increasing Agents

In some embodiments, the topical pharmaceutical composition comprises one or more viscosity-increasing agents. As used herein, a "viscosity increasing agent" refers to a compound or agent that increases the thickness of the aqueous component of the pharmaceutical composition. In some embodiments, the viscosity increasing agent comprises a cross-linked homopolymer of an acrylic acid. In some embodiments, the viscosity increasing agent comprises one or more of a carbomer homopolymer type A, carbomer homopolymer type B, or carbomer homopolymer type C. Carbomer homopolymers are commercially available, e.g., Carbopol® 981, Carbopol® 980, Carbopol® 71G, Carbopol® 971P, Carbopol® 974P, and Carbopol® 5984. In some embodiments, the viscosity increasing agent comprises Carbopol® 981.

In some embodiments, the viscosity increasing agent comprises acacia, alginic acid, bentonite, carboxymethyl cellulose, ethylcellulose, gelatin, hydroxyethyl cellulose, hydroxypropyl cellulose, magnesium aluminum silicate, methylcellulose, pectin, poloxamers, polyvinyl alcohol, sodium alginate, tragacanth, or xanthan gum. In some embodiments, the pharmaceutical composition comprises a cross-linked homopolymer of an acrylic acid (e.g., a Carbopol® carbomer homopolymer) and further comprises at least one additional viscosity increasing agent selected from the group consisting of acacia, alginic acid, bentonite, carboxymethylcellulose, ethylcellulose, gelatin, hydroxyethylcellulose, hydroxypropyl cellulose, magnesium aluminum silicate, methylcellulose, pectin, poloxamers, polyvinyl alcohol, sodium alginate, tragacanth, and xanthan gum.

Some viscosity increasing agents can also aid in the formation of emulsion. In some embodiments, the viscosity increasing agent acts as a secondary emulsifier when a polymeric emulsifier is used in the composition.

In some embodiments, the viscosity increasing agent(s) is present in an amount from about 0.1% to about 2% by weight of the composition, or from about 0.2% to about 1% by weight of the composition, or from about 0.4% to about 1% by weight of the composition. In some embodiments, the viscosity increasing agent is present in an amount of about 0.5%, about 0.55%, about 0.6%, about 0.65%, about 0.7%, about 0.75%, about 0.8%, about 0.85%, about 0.9%, about 0.95%, or about 1% by weight of the composition.

Polymeric Emulsifiers

In some embodiments, the topical pharmaceutical composition comprises a polymeric emulsifier. As used herein, a "polymeric emulsifier" refers to a predominantly high molecular weight copolymer of acrylic acid and alkyl acrylate. Typically, the copolymer is cross-linked. In some embodiments, the copolymer is cross-linked with allyl pentaerythritol. In some embodiments, the polymeric emulsifier comprises a copolymer of acrylic acid and C10-C30 alkyl acrylate cross-linked with allyl pentaerythritol. Polymeric emulsifiers are commercially available, e.g., Pemulen™ TR-1 and Pemulen™ TR-2. In some embodiments, the polymeric emulsifier comprises Pemulen™ TR-1 and/or TR-2. Other suitable polymeric emulsifiers are copolymers of acrylic acid and alkylmethacrylate, cross-linked with allyl ethers of pentaerythritol.

The topical pharmaceutical compositions of the present disclosure comprise a polymeric emulsifier in a low amount. In some embodiments, the polymeric emulsifier is present in an amount up to about 0.2% by weight of the composition, or up to about 0.1% by weight of the composition, or up to about 0.07% by weight of the composition, or up to about 0.06% by weight of the composition, or up to about 0.05% by weight of the composition. In some embodiments, the polymeric emulsifier is present in an amount from about 0.01% to about 0.2% by weight of the composition. In some embodiments, the polymeric emulsifier is present in an amount from about 0.01% to about 0.1% by weight of the composition. In some embodiments, the polymeric emulsifier is present in an amount from about 0.02% to about 0.1% by weight of the composition. In some embodiments, the polymeric emulsifier is present in an amount from about 0.02% to about 0.08% by weight of the composition. In some embodiments, the polymeric emulsifier is present in an amount from about 0.02% to about 0.06% by weight of the composition. In some embodiments, the polymeric emulsifier is present in an amount from about 0.01% to about 0.06% by weight of the composition. In some embodiments, the polymeric emulsifier is present in an amount from about 0.04% to about 0.06% by weight of the composition, e.g., from about 0.04% to about 0.05%. In some embodiments, the polymeric emulsifier is present in an amount of about 0.05% by weight of the composition.

Oil Component

In some embodiments, the topical pharmaceutical composition comprises an oil component. Examples of oils include, but are not limited to mineral oil; light mineral oil; petrolatum; fatty alcohols such as stearyl alcohol, cetyl alcohol, oleyl alcohol, and isostearyl alcohol; monocarboxylic acid esters such as isopropyl myristate, isopropyl palmitate, and benzyl benzoate; dicarboxylic acid esters such as diethyl sebacate, diisopropyl adipate, and dibutyl sebecate; and medium- or long-chain triglycerides. In some embodiments, the oil component comprises mineral oil, or a mixture of mineral oil and diethyl sebacate. In some embodiments, the oil component is a liquid oil.

In some embodiments, the oil component of a topical pharmaceutical composition of the present disclosure is present in an amount of about 20%, or less (such as 0.5-20%), by weight of the composition. In some embodiments, the oil component (e.g., mineral oil) is present in an amount up to about 10% by weight of the composition. In some embodiments, the oil component (e.g., mineral oil) is present in an amount up to about 7.5% by weight of the composition. In some embodiments, the oil component is present in an amount up to about 5% by weight of the composition, e.g., up to about 4.5%, up to about 4%, up to about 3.5%, up to about 3%, or up to about 2.5%. In some embodiments, the oil component is present in an amount from about 2% to about 4% by weight of the composition, e.g., about 2%, about 2.5%, about 3%, about 3.5%, or about 4% by weight of the composition. In some embodiments, the oil component is present in an amount from about 1% to about 5% by weight of the composition. In some embodiments, the oil component is present in an amount from about 1.5% to about 4% by weight of the composition. In some embodiments, the oil component is present in an amount from about 2% to about 4% by weight of the composition.

The ratio of the amount of oil to the total amount of viscosity agents and polymeric emulsifiers can be in the range from about 1.5:1 to about 20:1, or from about 2:1 to about 15:1, or from about 2:1 to about 10:1, or from about 2:1 to about 7.5:1, or from about 2:1 to about 5:1, or from about 2:1 to about 3:1.

Additional Components

In some embodiments, the topical pharmaceutical composition further comprises one or more additional components. For example, in some embodiments, the pharmaceutical composition comprises one or more humectants, moisturizing agents, antioxidants, preservatives, wetting agents, and/or neutralizing agents.

In some embodiments, the topical pharmaceutical composition comprises one or more moisturizing agents. Examples of suitable moisturizing agents include, but are not limited to, collagen, elastin, keratin, sodium hyaluronate, cholesterol, squalene, fatty acids, and fatty alcohols. In some embodiments, the moisturizing agent is a non-occlusive (e.g., non-oil) moisturizer. In some embodiments, the pharmaceutical composition comprises soluble collagen and sodium hyaluronate as moisturizing agents. In some embodiments, the one or more moisturizing agents are present in an amount from about 5% to about 20% by weight of the composition, e.g., from about 5% to about 15%, or from about 5% to about 10% by weight of the composition.

In some embodiments, the topical pharmaceutical composition comprises one or more humectants. Examples of suitable humectants include, but are not limited to, glycerin, sorbitol, xylitol, urea, ethylene glycol, hexylene glycol, polyethylene glycol, and propylene glycol. In some embodiments, the pharmaceutical composition comprises glycerin as a humectant. In some embodiments, the one or more humectants are present in an amount from about 5% to about 20% by weight of the composition, e.g., from about 5% to about 15%, from about 7% to about 15%, or from about 7% to about 10% by weight of the composition.

In some embodiments, the topical pharmaceutical composition comprises one or more preservatives. Examples of suitable preservatives include, but are not limited to, methyl paraben, ethyl paraben, propyl paraben, butyl paraben, benzyl alcohol, cetyl alcohol, steryl alcohol, benzoic acid, sorbic acid, and quaternary ammonium compounds. In some embodiments, the pharmaceutical composition comprises methyl paraben, propyl paraben, benzyl alcohol, or a combination thereof as the preservative(s). In some embodiments, the one or more preservatives are present in an amount from about 0.25% to about 5% by weight of the composition, e.g., from about 0.5% to about 3%, from about 0.5% to about 1.5%, or from about 0.25% to about 1% by weight of the composition.

In some embodiments, the topical pharmaceutical composition comprises one or more antioxidants. Examples of suitable antioxidants include, but are not limited to, alpha-tocopherol, ascorbic acid, butylhydroxyanisole (BHA), butylated hydoxytoluene (BHT), monothioglycerol, potassium metabisulfite, sodium ascorbate, sodium bisulfite, sodium metabisulfite, and sodium sulfite. In some embodiments, the pharmaceutical composition comprises BHT as an antioxidant. In some embodiments, the one or more antioxidants are present in an amount from about 0.1% to about 2% by weight of the composition, e.g., from about 0.15% to about 1%, from about 0.2% to about 1%, or from about 0.2% to about 0.6% by weight of the composition.

In some embodiments, the topical pharmaceutical composition comprises one or more wetting agents. In some embodiments, the wetting agent is included for aiding in the dispersal or suspension of the active agent in an aqueous carrier. In some embodiments, the wetting agent is a surfactant, e.g., a non-ionic surfactant. Examples of suitable wetting agents include, but are not limited to, octoxynol-9, nonoxynol-9, polysorbate 20, polysorbate 40, polysorbate 60, polysorbate 80, sorbitan monolaurate, sorbitan monooleate, sorbitan monopalmitate, sorbitan monostearate, and sorbitan trioleate. In some embodiments, the pharmaceutical composition comprises octoxynol-9 as a wetting agent. In some embodiments, the wetting agent is present in an amount from about 0.05% to about 0.5% by weight of the composition, or from about 0.1% to about 0.5% by weight of the composition, or from about 0.05% to about 0.4% by weight of the composition, or from about 0.1% to about 0.4% by weight of the composition, or from about 0.1% to about 0.3% by weight of the composition. In some embodiments, the pharmaceutical composition comprises a non-ionic or anionic surfactant in an amount greater than 0.05% by weight of the composition. In some embodiments, the pharmaceutical composition comprises a non-ionic or anionic surfactant in an amount greater than 0.1% by weight of the composition. In some embodiments, the pharmaceutical composition does not comprise a non-ionic surfactant. In some embodiments, the pharmaceutical composition does not comprise an anionic surfactant.

In some embodiments, the topical pharmaceutical composition comprises a neutralizing agent. In some embodiments, the neutralizing agent maintains the pH of the pharmaceutical composition at a pH from about 5-6. Suitable neutralizing agents include, but are not limited to, trolamine (triethanolamine), sodium hydroxide, and potassium hydroxide. In some embodiments, the pharmaceutical composition comprises trolamine as a neutralizing agent.

In some embodiments, the topical pharmaceutical composition is an aqueous composition comprising water, e.g., purified water. In some embodiments, the composition comprises at least 50% water by weight of the composition, e.g., at least 60%, at least 65%, at least 70%, at least 75%, at least 80%, at least 85%, or at least 90% water by weight of the composition.

In some embodiments, a topical pharmaceutical composition for treating a skin condition or disorder comprises:
an active agent that is useful for treating the skin condition or disorder in an amount from about 0.001% to about 1% by weight of the composition;
a viscosity increasing agent in an amount from about 0.2% to about 1% by weight of the composition;
a polymeric emulsifier in an amount from about 0.01% to about 1% by weight of the composition;
an oil component in an amount from about 1% to about 4% by weight of the composition;
one or more moisturizing agents in an amount from about 5% to about 20% by weight of the composition;
one or more humectants in an amount from about 5% to about 20% by weight of the composition;
one or more preservatives in an amount from about 0.25% to about 5% by weight of the composition;
one or more antioxidants in an amount from about 0.1% to about 2% by weight of the composition;
one or more wetting agents in an amount from about 0.05% to about 0.5% by weight of the composition;
a neutralizing agent; and
water;
wherein the composition is formulated as a lotion.

In some embodiments, the active agent is a retinoid, e.g., retinol, retinal, tretinoin, isotretinoin, alitretinoin, etretinate, acitretin, adapalene, bexarotene, or tazarotene. In some embodiments, the active agent is a corticosteroid, e.g., clobetasol, halobetasol, betamethasone, fluocinonide, diflorasone, desoximetasone, mometasone, flurandrenolide, halcinonide, amcinonide, budesonide, desonide, beclomethasone, triamcinolone, fluticasone, hydrocortisone, or fluocinolone. In some embodiments, the active agent is an antibiotic, e.g., clindamycin, erythromycin, natamycin, neomycin, mupirocin, fusidic acid, minocycline, dapsone, or tetracycline. In some embodiments, the active agent is an anti-inflammatory agent, e.g., metronidazole, ibuprofen, indomethacin, diclofenac, or naproxen.

In some embodiments, a topical pharmaceutical composition for treating a skin condition or disorder is formulated as a lotion and comprises:
tretinoin an amount from about 0.001% to about 1% by weight of the composition;
a viscosity increasing agent in an amount from about 0.2% to about 1% (e.g., from about 0.6% to about 1%) by weight of the composition, wherein the viscosity increasing agent is carbomer homopolymer type A (one such carbomer homopolymer is known by the trade name Carbopol® 981);
a polymeric emulsifier in an amount from about 0.01% to about 1% (e.g., from about 0.04% to about 0.06%) by weight of the composition, wherein the polymeric emulsifier is a carbomer copolymer type B (one such carbomer copolymer is known by the trade name Pemulen® TR-1);
an oil component in an amount from about 2% to about 4% by weight of the composition, wherein the oil component is a mineral oil;
one or more moisturizing agents in an amount from about 5% to about 20% by weight of the composition, wherein the moisturizing agents are sodium hyaluronate, soluble collagen, or a combination thereof;
a humectant in an amount from about 5% to about 20% by weight of the composition, wherein the humectant is glycerin;
one or more preservatives in an amount from about 0.25% to about 5% by weight of the composition, wherein the preservatives are benzyl alcohol, methyl paraben, or a combination thereof;
an antioxidant in an amount from about 0.1% to about 2% by weight of the composition, wherein the antioxidant is butylated hydroxytoluene;
a wetting agent in an amount from about 0.05% to about 0.5% by weight of the composition, wherein the wetting agent is octoxynol-9;
a neutralizing agent, wherein the neutralizing agent is trolamine; and
water.

In some embodiments, the topical pharmaceutical composition consists essentially of a therapeutically effective amount of an active agent that is useful for treating the skin condition or disorder (such as, but not limited to, a retinoid, a corticosteroid, an antibiotic, or an anti-inflammatory agent); a viscosity increasing agent; a polymeric emulsifier; an oil component; water; and one or more humectants, moisturizing agents, antioxidants, preservatives, wetting agents, and/or neutralizing agents. In some embodiments, the pharmaceutical composition consists essentially of a retinoid, a corticosteroid, an antibiotic, or an anti-inflammatory agent in an amount from 0.001% to 1% by weight of the composition; a viscosity increasing agent; a polymeric emulsifier; an oil component; water; a humectant; a moisturizing agent; an antioxidant; a wetting agent; and optionally, a neutralizing agent and/or a preservative.

In some embodiments, the topical pharmaceutical composition consists of a therapeutically effective amount of an active agent that is useful for treating the skin condition or disorder (such as, but not limited to, a retinoid, a corticosteroid, an antibiotic, or an anti-inflammatory agent); a viscosity increasing agent; a polymeric emulsifier; an oil component; water; and one or more humectants, moisturizing agents, antioxidants, preservatives, wetting agents, and/or neutralizing agents. In some embodiments, the pharmaceutical composition consists of a retinoid, a corticosteroid, an antibiotic, or an anti-inflammatory agent in an amount from 0.001% to 1% by weight of the composition; a viscosity increasing agent; a polymeric emulsifier; an oil component; water; a humectant; a moisturizing agent; an antioxidant; a wetting agent; and optionally, a neutralizing agent and/or a preservative.

In some embodiments, a topical pharmaceutical composition for treating a skin condition or disorder is formulated as a lotion and consists essentially of:

an active agent that is useful for treating the skin condition or disorder in an amount from about 0.001% to about 1% by weight of the composition, wherein the active agent is a retinoid, a corticosteroid, an antibiotic, or an anti-inflammatory agent;

a viscosity increasing agent in an amount from about 0.2% to about 1% (e.g., from about 0.6% to about 1%) by weight of the composition;

a polymeric emulsifier in an amount from about 0.01% to about 1% (e.g., from about 0.04% to about 0.06%) by weight of the composition;

an oil component in an amount from about 2% to about 4% by weight of the composition;

one or more moisturizing agents in an amount from about 5% to about 20% by weight of the composition;

one or more humectants in an amount from about 5% to about 20% by weight of the composition;

one or more antioxidants in an amount from about 0.1% to about 2% by weight of the composition;

one or more wetting agents in an amount from about 0.05% to about 0.5% by weight of the composition;

optionally, one or more preservatives in an amount from about 0.25% to about 5% by weight of the composition;

optionally, a neutralizing agent; and water.

In some embodiments, a topical pharmaceutical composition for treating a skin condition or disorder is formulated as a lotion and consists essentially of:

tretinoin an amount from about 0.001% to about 1% by weight of the composition;

a viscosity increasing agent in an amount from about 0.2% to about 1% (e.g., from about 0.6% to about 1%) by weight of the composition, wherein the viscosity increasing agent is carbomer homopolymer type A (one such carbomer homopolymer is known by the trade name Carbopol® 981);

a polymeric emulsifier in an amount from about 0.01% to about 0.1% (e.g., from about 0.04% to about 0.06%) by weight of the composition, wherein the polymeric emulsifier is a carbomer copolymer type B (one such carbomer copolymer is known by the trade name Pemulen® TR-1);

an oil component in an amount from about 2% to about 4% by weight of the composition, wherein the oil component is a mineral oil;

one or more moisturizing agents in an amount from about 5% to about 20% by weight of the composition, wherein the moisturizing agents are sodium hyaluronate, soluble collagen, or a combination thereof;

a humectant in an amount from about 5% to about 20% by weight of the composition, wherein the humectant is glycerin;

an antioxidant in an amount from about 0.1% to about 2% by weight of the composition, wherein the antioxidant is butylated hydroxytoluene;

a wetting agent in an amount from about 0.05% to about 0.5% by weight of the composition, wherein the wetting agent is octoxynol-9;

optionally, one or more preservatives in an amount from about 0.25% to about 5% by weight of the composition, wherein the preservatives are benzyl alcohol, methyl paraben, or a combination thereof;

optionally, a neutralizing agent, wherein the neutralizing agent is trolamine; and water.

In some embodiments, the topical pharmaceutical composition consists essentially of: tretinoin, benzyl alcohol, butylated hydroxytoluene, carbomer copolymer type B (e.g., Pemulen® TR-1), carbomer homopolymer type A (e.g., Carbopol® 981), glycerin, mineral oil, octoxynol-9, purified water, sodium hyaluronate, soluble collagen, and optionally, a neutralizing agent and/or a preservative. In some embodiments, the topical pharmaceutical composition consists essentially of: tretinoin, benzyl alcohol, butylated hydroxytoluene, carbomer copolymer type B (e.g., Pemulen® TR-1), carbomer homopolymer type A (e.g., Carbopol® 981), glycerin, mineral oil, nitrogen, octoxynol-9, purified water, sodium hyaluronate, soluble collagen, and optionally, a neutralizing agent and/or a preservative. In some embodiments, the pharmaceutical composition consists essentially of: tretinoin in an amount of 0.05% by weight of the composition, benzyl alcohol, butylated hydroxytoluene, carbomer copolymer type B (e.g., Pemulen® TR-1), carbomer homopolymer type A (e.g., Carbopol® 981), glycerin, mineral oil, nitrogen, octoxynol-9, purified water, sodium hyaluronate, soluble collagen, and optionally, a neutralizing agent (such as trolamine) and/or a preservative (such as methylparaben).

In some embodiments, the topical pharmaceutical composition consists of: tretinoin, benzyl alcohol, butylated hydroxytoluene, carbomer copolymer type B (e.g., Pemulen® TR-1), carbomer homopolymer type A (e.g., Carbopol® 981), glycerin, mineral oil, octoxynol-9, purified water, sodium hyaluronate, soluble collagen, and optionally, a neutralizing agent and/or a preservative. In some embodiments, the topical pharmaceutical composition consists of: tretinoin, benzyl alcohol, butylated hydroxytoluene, carbomer copolymer type B (e.g., Pemulen® TR-1), carbomer homopolymer type A (e.g., Carbopol® 981), glycerin, mineral oil, nitrogen, octoxynol-9, purified water, sodium hyaluronate, soluble collagen, and optionally, a neutralizing agent and/or a preservative. In some embodiments, the pharmaceutical composition consists of: tretinoin in an amount of 0.05% by weight of the composition, benzyl alcohol, butylated hydroxytoluene, carbomer copolymer type B (e.g., Pemulen® TR-1), carbomer homopolymer type A (e.g., Carbopol® 981), glycerin, mineral oil, nitrogen, octoxynol-9, purified water, sodium hyaluronate, soluble collagen, and optionally, a neutralizing agent (such as trolamine) and/or a preservative (such as methylparaben).

IV. Methods of Treating Skin Conditions

In another aspect, methods for the treatment of a skin condition or disorder are provided. In some embodiments, the skin condition or disorder is acne (e.g., acne vulgaris); psoriasis (e.g., plaque psoriasis, guttate psoriasis, inverse psoriasis, pustular psoriasis, erythrodermic psoriasis, nail psoriasis, or psoriatic arthritis); dermatitis such as atopic, contact, or hand dermatitis, eczema, seborrheic dermatitis, rash, or poison ivy dermatitis; rosacea; or skin lesions. In some embodiments, the topical pharmaceutical composition (e.g., a composition comprising a corticosteroid, an antibiotic, an anti-inflammatory agent, or a retinoid) is used for the treatment of acne. In some embodiments, a topical pharmaceutical composition comprising a retinoid (e.g., tretinoin) is used for the treatment of acne, e.g., acne vulgaris. In some embodiments, a topical pharmaceutical composition comprising a retinoid (e.g., tretinoin) is used for the treatment of facial acne vulgaris, e.g., facial acne vulgaris of mild to moderate severity.

In some embodiments, the topical pharmaceutical composition (e.g., a composition comprising a corticosteroid, an antibiotic, an anti-inflammatory agent, or a retinoid) is used cosmetically, e.g., for reducing the appearance of fine lines, wrinkles, fine wrinkling, blotches, hyperpigmentation, skin roughness, or for the improvement of skin tone. In some embodiments, the topical pharmaceutical composition comprises a retinoid, e.g., retinol, retinal, tretinoin, isotretinoin, alitretinoin, etretinate, acitretin, adapalene, bexarotene, or tazarotene.

In some embodiments, a topical pharmaceutical composition as disclosed herein (e.g., a composition comprising a corticosteroid, an antibiotic, an anti-inflammatory agent, or a retinoid) is administered to a subject in need thereof for at least 1, 2, 3, 4, 5, 6, or 7 days or longer, e.g., for at least 1, 2, 3, 4, 5, 6, 7, 8, 9, or 10 weeks or longer. In some embodiments, a topical pharmaceutical composition as disclosed herein is administered to a subject in need thereof for a period of 1-30 days, e.g., 7-30 days, 7-28 days, 7-21 days, 7-14 days, 10-30 days, 14-30 days, or 14-28 days. In some embodiments, a topical pharmaceutical composition as disclosed herein is administered to a subject in need thereof for a period of 1-30 weeks or longer, e.g., 1-20, 1-10, 1-8, 2-20, 2-15, 2-12, 2-10, 2-8, 4-30, 4-20, 4-12, 4-8, 6-30, 6-20, 6-12, 8-30, 8-24, 8-12, 10-30, 10-20, 15-30 weeks, or longer.

In some embodiments, a topical pharmaceutical composition as disclosed herein is administered to a subject in need thereof for a period of treatment longer than 2 weeks, longer than 3 weeks, longer than 4 weeks, longer than 1 month, longer than 2 months, longer than 3 months, longer than 4 months, longer than 5 months, or longer than 6 months. In some embodiments, a topical pharmaceutical composition as disclosed herein is administered to a subject in need thereof for a period of treatment up to 2 weeks, up to 3 weeks, up to 4 weeks, up to 1 month, up to 2 months, up to 3 months, up to 4 months, up to 5 months, up to 6 months, or until clearance of the skin disorder or condition (e.g., acne, psoriasis, dermatitis, rash, etc.) is achieved. In some embodiments, a topical pharmaceutical composition as disclosed herein until clearance of the skin disorder or condition (e.g., acne, psoriasis, dermatitis, rash, etc.) is achieved. In some embodiments, the topical pharmaceutical composition is applied to the affected area or areas of skin one, two, or three times a day. In some embodiments, the topical pharmaceutical composition is applied to the affected area or areas of skin once daily. In some embodiments, the topical pharmaceutical composition is applied to the affected area or areas of skin twice daily. In some embodiments, the topical pharmaceutical composition is applied to the affected area or areas of skin up to two, three, or four times a day.

In some embodiments, the topical pharmaceutical composition comprising a retinoid (e.g., tretinoin) is administered topically once daily or twice daily, e.g., for the treatment of a skin condition or disorder such as acne, e.g., acne vulgaris. In some embodiments, a topical pharmaceutical composition comprising a retinoid (e.g., tretinoin) is administered once daily or twice daily (e.g., in the morning and/or evening) to afflicted areas of the skin, e.g., to areas of the skin where lesions occur. In some embodiments, a topical pharmaceutical composition comprising a retinoid (e.g., tretinoin) is administered three or four times daily (e.g., in the morning and/or evening) to afflicted areas of the skin, e.g., to areas of the skin where lesions occur.

In some embodiments, a topical pharmaceutical composition as disclosed herein (e.g., a composition comprising a corticosteroid, an antibiotic, an anti-inflammatory agent, or a retinoid) is administered to a subject in need thereof in two or more treatment periods, in which the treatment periods are separated by a period of time in which the topical pharmaceutical composition is not administered. For example, in some embodiments, a first treatment period is administered for a period of 1, 2, 3, 4, 5, 6, or 7 days or longer, e.g., least 1, 2, 3, 4, 5, 6, 7, 8, 9, or 10 weeks or longer, then treatment is stopped for at least 1, 2, 3, 4, 5, 6, or 7 days or longer (e.g., for at least 1, 2, 3, 4, 5 weeks or longer) before the second treatment period (e.g., a period of 1, 2, 3, 4, 5, 6, or 7 days or longer, e.g., least 1, 2, 3, 4, 5, 6, 7, 8, 9, or 10 weeks or longer) is administered.

In some embodiments, a topical pharmaceutical composition as disclosed herein (e.g., a composition comprising a corticosteroid, an antibiotic, an anti-inflammatory agent, or a retinoid) is administered in combination with one or more other therapies for the skin disorder or condition. As a non-limiting example, in some embodiments, a topical pharmaceutical composition comprising retinoid (e.g., tretinoin) as disclosed herein is administered in combination with one or more other therapies for the treatment of acne, such as an antibiotic (e.g., clindamycin, erythromycin, natamycin, neomycin, mupirocin, fusidic acid, minocycline, dapsone), an anti-inflammatory agent (e.g., metronidazole), or a composition comprising benzoyl peroxide.

In some embodiments, a topical pharmaceutical composition as disclosed herein is administered to an adult subject. In some embodiments, a topical pharmaceutical composition as disclosed herein is administered to a juvenile subject.

V. Kits

In another aspect, kits for the treatment of a skin condition or disorder are provided. In some embodiments, the kit comprises a topical pharmaceutical composition (e.g., a composition comprising a corticosteroid, an antibiotic, an anti-inflammatory agent, or a retinoid) as disclosed herein. In some embodiments, the kit comprises a topical pharmaceutical composition comprising a retinoid. In some embodiments, the kit comprises a topical pharmaceutical composition comprising tretinoin (e.g., in an amount of about 0.05% by weight of the composition).

In some embodiments, the kit is for use in the treatment of a skin condition or disorder that is acne (e.g., acne vulgaris); psoriasis (e.g., plaque psoriasis, guttate psoriasis, inverse psoriasis, pustular psoriasis, erythrodermic psoriasis, nail psoriasis, or psoriatic arthritis); dermatitis such as atopic, contact, or hand dermatitis, eczema, seborrheic dermatitis, rash, or poison ivy dermatitis; rosacea; or skin lesions. In some embodiments, the kit is for use in the treatment of acne, e.g., acne vulgaris.

In some embodiments, the kit is for cosmetic use, e.g., for reducing the appearance of fine lines, wrinkles, fine wrinkling, blotches, hyperpigmentation, skin roughness, or for the improvement of skin tone.

In some embodiments, the kit further comprises a product insert and/or instructions for administering the topical pharmaceutical composition, e.g., according to the methods disclosed herein. While instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips, USB drives, and SD cards), optical media (e.g., CD-ROM and DVDs) and the like. Such media may include addresses to internet sites that provide such instructional materials.

In some embodiments, the kit further comprises one or more other agents for use in the treatment of the skin disorder or condition. The topical pharmaceutical composition and the one or more other agents can be administered concurrently or sequentially.

VI. Vehicles for Topical Compositions

In another aspect, a vehicle is provided for use as a vehicle in making topical compositions. The vehicle comprises an oil-in-water emulsion and comprises: (a) a polymer having hydrophobic and hydrophilic groups, the polymer being selected from the group consisting of polymeric viscosity-increasing agents in an amount of about 0.1-2% by weight of the vehicle, polymeric emulsifiers in an amount of about 0.01-0.2% by weight of the vehicle, and combinations thereof; (b) an oil component in an amount of 20%, or less (such as 0.5-20%), by weight of the vehicle; and (c) water. Other amounts of these ingredients as disclosed herein above are also suitable.

In another aspect, the ratio of the amount of oil component to the total amount of viscosity agents and polymeric emulsifiers can be in the range from about 1.5:1 to about 20:1, or from about 1.5:1 to about 10:1, or from about 1.5:1 to about 5:1, or from about 3:1 to about 20:1, or from about 3:1 to about 10:1, or from about 5:1 to about 20:1, or from about 5:1 to about 10:1. Other ratios as disclosed herein above are also suitable.

In another aspect, the oil component is a liquid oil.

In still another aspect, the oil-in-water emulsion is stable for up to 1 hour, 2 hours, 4 hours, 6 hours, 12 hours, one day, two days, 3 days, one week, two weeks, three weeks, or four weeks.

VII. Examples

The following examples are offered to illustrate, but not to limit, the claimed invention.

Example 1. Exemplary Tretinoin Lotion

This example provides the composition of an exemplary tretinoin pharmaceutical composition of the present disclosure that is formulated as a lotion, in comparison to the composition of a commercially available tretinoin gel composition (ATRALIN® (tretinoin) gel, 0.05%).

TABLE 1

Composition of tretinoin lotion and ATRALIN ® gel

| Ingredient | Function | Tretinoin lotion (%) | ATRALIN gel (%) |
|---|---|---|---|
| Tretinoin | Anti-acne | 0.05 | 0.05 |
| Glycerin | Humectant | 9.63 | 9.63 |
| Soluble collagen | Moisturizing agent | 8.00 | 8.00 |
| Carbopol ® 980 | Viscosity increasing agent | — | 0.90 |
| Carbomer homopolymer type A (Carbopol ® 981) | Viscosity increasing agent | 0.70 | — |
| Carbomer copolymer type B (Pemulen ® TR-1) | Emulsifier | 0.05 | — |
| Octoxynol-9 | Wetting agent | 0.12 | 0.12 |
| Sodium hyaluronate | Moisturizing agent | 0.011 | 0.011 |
| Methyl paraben | Antimicrobial preservative | 0.20 | 0.20 |
| Butylated Hydroxytoluene | Anti-oxidant | 0.21 | 0.21 |
| Benzyl alcohol | Antimicrobial preservative | 0.50 | 0.50 |
| Propyl paraben | Antimicrobial preservative | — | 0.03 |
| Mineral oil | Emollient | 2.00 | — |
| Trolamine | Neutralizing agent | pH 5.0-6.0 | pH 5.0-6.0 |
| Water | Carrier | qs 100 | qs 100 |

Example 2. Exemplary Tretinoin Composition

This example provides an exemplary manufacturing process for making a tretinoin pharmaceutical lotion composition as disclosed in Table 1.

A polymeric phase is made. In a suitable manufacturing vessel, purified water, Carbomer homopolymer type A (Carbopol 981), and Carbomer copolymer type B (Pemulen TR-1) are added and mixed until the contents are dispersed. Next, mineral oil is added and mixed.

Next, a moisturizing agent is prepared. In a separate suitable vessel, sodium hyaluronate and purified water are added and mixed until the sodium hyaluronate is dissolved. The contents of the vessel containing the sodium hyaluronate is added to the polymeric phase and the contents are mixed.

Next, a preservative phase is prepared. In a separate suitable vessel, glycerin is added and mixed while heating. Next, methylparaben and benzyl alcohol are added to the vessel and the contents are mixed until dissolved. The preservative phase is added to the vessel containing the polymeric phase, rinsed with glycerin, and mixed.

Next, an active phase is prepared. In a separate suitable vessel, purified water and glycerin are added, mixed, and blanketed with nitrogen. Next, under yellow lighting, butylated hydroxytoluene, octoxynol 9, and tretinoin are added to the vessel. The contents are mixed and then milled with recirculation. Under yellow lighting, the contents of the vessel containing the active phase are transferred to the vessel containing the polymeric phase, rinsed with purified water, and mixed. Next, under yellow lighting, soluble collagen is added to the vessel containing the polymeric phase and mixed.

Next, a neutralizing agent is prepared. In a separate suitable vessel, trolamine and purified water are added and mixed to form a solution having a pH of 5.0-6.0.

Next, under yellow lighting, the contents of the vessel containing the polymeric phase are transferred to a new vessel, rinsed with purified water, agitated, and recirculated under nitrogen. The pH of the composition is determined and the pH is adjusted with the neutralizing agent as necessary. The contents of the vessel are then transferred to a bulk storage container for filling secondary packaging.

Viscosity is determined in accordance with the current USP general chapter for viscosity determination. The test conditions include a temperature of 23°+2° C., spindle 27, and a speed of 12 rpm. Typical viscosity of compositions of the present invention are in the range of about 9000 to about 11000 cP. Depending on the amounts of various components, viscosity values can range from about 2500 cP to about 18000 cP.

Example 3. Improved Properties of Topical Pharmaceutical Compositions Comprising Tretinoin This example provides clinical data demonstrating the surprisingly superior properties of a tretinoin lotion formulated according to the present disclosure. A tretinoin lotion formulated as disclosed in Table 1 above was tested in comparison to a vehicle lotion and in comparison to a commercially available tretinoin gel, ATRALIN® (0.05% tretinoin). As described herein, the tretinoin lotion demonstrated an unexpectedly improved local tolerability (i.e., low irritation) profile as compared to ATRALIN® gel.

Clinical Studies

The safety and efficacy of once daily use of tretinoin lotion for the treatment of acne vulgaris were assessed in two prospective, multicenter, randomized, double-blind clinical trials in subjects 9 years and older with moderate to severe acne vulgaris. The trials compared 12 weeks of treatment with tretinoin lotion to the vehicle lotion. ATRALIN® gel and ATRALIN® gel vehicle were evaluated clinically in separate studies from the tretinoin lotion. The co-primary efficacy endpoints of absolute change in non-inflammatory lesion count, absolute change in inflammatory lesion count, and "treatment success" were assessed at Week 12. Treatment success was defined as at least a 2-grade improvement from Baseline in the Evaluators Global Severity Score (EGSS) score and an EGSS score equating to "clear" or "almost clear." Table 2 sets forth the EGSS scale that is used to assess the severity of the disease state. Table 3 lists the efficacy results for trials 1 and 2.

TABLE 2

Evaluator's Global Severity Score (EGSS)

| Score | Grade | Description |
|---|---|---|
| 0 | Clear | Normal, clear skin with no evidence of acne |
| 1 | Almost Clear | Rare noninflammatory lesions present, with rare noninflamed papules (papules must be resolving and may be hyperpigmented, though not pink-red) |
| 2 | Mild | Some noninflammatory lesions are present, with few inflammatory lesions (papules/pustules only; no nodulocystic lesions) |
| 3 | Moderate | Noninflammatory lesions predominate, with multiple inflammatory lesions evident: several to many comedones and papules/pustules, and there may or may not be 1 nodulocystic lesion |
| 4 | Severe | Inflammatory lesions are more apparent, many comedones and papules/pustules, there may or may not be up to 2 nodulocystic lesions |

TABLE 3

Results of Phase 3 Trials in Subjects with Acne Vulgaris at Week 12

| | Tretinoin Lotion | Tretinoin Lotion Vehicle | ATRALIN® Gel | ATRALIN® Gel Vehicle |
|---|---|---|---|---|
| Evaluators Global Severity Score (EGSS) | | | | |
| Trial 1 | | | | |
| Clear or Almost Clear and 2-Grade Reduction from Baseline | 16.5% | 6.9% | 21% | 12% |
| Non-Inflammatory Facial Lesions | | | | |
| Mean Absolute Reduction | 17.8 | 10.6 | 21.8 | 10.3 |
| Mean Percent Reduction | 47.5% | 27.3% | 43% | 21% |
| Inflammatory Facial Lesions | | | | |
| Mean Absolute Reduction | 13.1 | 10.2 | 9.7 | 5.8 |
| Mean Percent Reduction | 50.9% | 40.4% | 41% | 26% |
| EGSS | | | | |
| Trial 2 | | | | |
| Clear or Almost Clear and 2-Grade Reduction from Baseline | 19.8% | 12.5% | 23% | 14% |
| Non-Inflammatory Facial Lesions | | | | |
| Mean Absolute Reduction | 21.9 | 13.9 | 18.7 | 10.8 |
| Mean Percent Reduction | 45.6% | 31.9% | 37% | 20% |
| Inflammatory Facial Lesions | | | | |
| Mean Absolute Reduction | 13.9 | 10.7 | 7.0 | 4.0 |
| Mean Percent Reduction | 53.4% | 41.5% | 30% | 17% |

Improvement in Local Tolerability

Increases in signs and symptoms of local tolerability with use of a retinoid in the instant invention is an unexpected outcome. As detailed below, it has been surprisingly found that formulating tretinoin as a lotion according to the methods disclosed herein resulted in a marked improvement in the tolerability profile of the tretinoin, as compared to the tolerability profile of tretinoin formulated as a gel.

Table 4 below summarizes the treatment emergent adverse events (TEAEs) reported in each of the programs using data from pivotal phase 3 clinical studies as described above. The preferred terms are coded to the Medical Dictionary for Regulatory Activities (MedDRA) current at the time of each study.

TABLE 4

Comparison of Treatment Emergent Adverse Events from Tretinoin Lotion and ATRALIN Gel Clinical Studies

| System Organ Class (SOC) and Preferred Term (PT) | Tretinoin Lotion (N = 767) | Tretinoin Vehicle Lotion (N = 783) | MedDRA (SOC) | Atralin Gel (N = 674) | Atralin Gel Vehicle (N = 487) |
|---|---|---|---|---|---|
| | TEASs by MedDRA SOC and PT (Safety Population) | | | Overall Summary for AE's (Safety Subjects) | |
| General disorders and administration site conditions | 78 (10.2%) | 29 (3.7%) | Skin and subcutaneous tissue disorders<br>Dry Skin | 208 (31%)<br>109 (16%) | 25 (5%)<br>8 (2%) |
| Application site dryness | 29 (3.8%) | 1 (0.1%) | Pain of Skin | 7 (1%) | 0 |
| Application site pain | 25 (3.3%) | 3 (0.4%) | Erythema | 47 (7%) | 1 (<1%) |
| Application site erythema | 12 (1.6%) | 1 (0.1%) | Pruritus +Pruritus generalized | 12 (2%) | 3 (1%) |
| Application site pruritus | 7 (0.9%) | 4 (0.5%) | Skin irritation | 3 (<1%) | 0 |
| Application site irritation | 7 (0.9%) | 1 (0.1%) | Skin exfoliation + skin desquamation | 28 (4%) | 2 (<1%) |
| Application site exfoliation | 6 (0.8%) | 3 (0.4%) | Dermatitis + D. exfolative + D. seborrheic | 39 (6%) | 4 (1%) |
| Application site dermatitis | 3 (0.4%) | 1 (0.1%) | | | |
| Application site rash | 3 (0.4%) | 0 | Face edema + skin swelling | 2 (<1%) | 0 |
| Application site swelling | 2 (0.3%) | 0 | Ulcer | 0 | 0 |
| Application site ulcer | 2 (0.3%) | 0 | Skin burning sensation | 53 (8%) | 8 (2%) |
| Application site burn | 1 (0.1%) | 0 | Skin hypopigmentation | 1 (<1%) | 0 |
| Application site discoloration | 1 (0.1%) | 0 | Urticaria | 1 (<1%) | 0 |
| Application site acne | 0 | 2 (0.3%) | Dermatitis contact | 6 (1%) | 1 (1%) |
| Application site urticarial | 0 | 1 (0.1%) | Eczema + Ecz nummular + Ecz weeping | 0 | 1 (<1%) |
| Skin and subcutaneous tissue disorders | 5 (0.7%) | 6 (0.8%) | Pityriasis rosacea<br>Acne | 1 (<1%)<br>3 (<1%) | 0<br>1 (<1%) |
| Dermatitis contact | 2 (0.3%) | 1 (0.1%) | Rash + Rash generalized + Rash macular + Rash pruritic + Rash scaly | 21 (3%) | 1 (<1%) |
| Eczema | 1 (0.1%) | 1 (0.1%) | | | |
| Pityriasis rosea | 1 (0.1%) | 0 | | | |
| Acne | 0 | 1 (0.1%) | | | |
| Rash | 0 | 1 (0.1%) | | | |

As shown in Table 4, tretinoin lotion demonstrated superior tolerability over ATRALIN® gel for several key signs and symptoms of local irritation listed below. Note that the comparisons are presented as reported percentages of adverse events ("AEs") for tretinoin lotion vs. ATRALIN® gel.

Dry skin (3.8% vs. 16%)
Burning (0.1% vs. 8%)
Erythema (1.6% vs. 7%)
Exfoliation (0.8% vs. 4%)

Review of data from literature revealed another surprising finding. Counter to traditional teachings, the addition of moisturizing and emolliency-imparting ingredients like mineral oil or medium chain triglycerides in a topical pharmaceutical composition does not inherently translate into an improved tolerability profile. For example, data obtained from clinical testing of a commercially available tazarotene gel and a commercially available tazarotene cream show that incidences of dry skin, erythema and desquamation (exfoliation) increased in the cream formulation of 0.1% tazarotene relative to a gel formulation of 0.1% tazarotene. The qualitative compositions of a commercially available tazarotene gel and cream are shown in Table 5 below.

TABLE 5

Qualitative Composition of Tazarotene Gel and Cream

| Tazarotene Gel, 0.1% | Tazarotene Cream, 0.1% |
|---|---|
| tazarotene 0.1% (w/w) | tazarotene 0.1% (w/w) |
| ascorbic acid | benzyl alcohol |
| benzyl alcohol | carbomer 1342 |
| butylated hydroxyanisole | carbomer homopolymer Type B |
| butylated hydroxytoluene | edetate disodium |
| carbomer homopolymer Type B | medium chain triglycerides |
| edetate disodium | mineral oil |
| hexylene glycol | purified water |
| poloxamer 407 | sodium hydroxide |
| polyethylene glycol 400 | sodium thiosulfate |
| polysorbate 40 | sorbitan monooleate |
| purified water | |
| tromethamine | |

Source: Product inserts for TAZORAC ® Gel and Cream, Allergan (Irvine, CA)

Table 6 below shows a comparison of key adverse events associated with local tolerability for the two retinoid molecules (tretinoin ("Tret") and tazarotene ("Taz")), each formulated in a gel base and in a lotion or a cream base with emollients.

TABLE 6

Comparison of Key Local Tolerability Adverse Events

| | Tret lotion | Tret vehicle | Atralin gel | Atralin vehicle | Taz cream | Taz cream vehicle | Taz gel | Taz gel vehicle |
|---|---|---|---|---|---|---|---|---|
| % of subjects reporting application site dryness/dry skin | 3.8 | 0.1 | 16 | 2 | 26.9 | 2.6 | 19.7 | 4.7 |
| % of subjects reporting erythema | 1.6 | 0.1 | 7 | 0.2 | 20.8 | 2.1 | 17.7 | 0 |

TABLE 6-continued

Comparison of Key Local Tolerability Adverse Events

|  | Tret lotion | Tret vehicle | Atralin gel | Atralin vehicle | Taz cream | Taz cream vehicle | Taz gel | Taz gel vehicle |
|---|---|---|---|---|---|---|---|---|
| % of subjects reporting skin exfoliation/desquamation | 0.8 | 0.4 | 4 | 0.4 | 29.2 | 2.8 | 28.1 | 2 |
| % of subjects reporting burning/stinging | 0.1 | 0 | 8 | 2 | 14.2 | 0.7 | 24.7 | 2.7 |

Sources for data:
Tretinoin ("Tret") lotion, Tret vehicle, Atralin gel, and Atralin vehicle - Table 4
Tazarotene ("Taz") cream and Taz cream vehicle - FDA Summary Basis of Approval for NDA 21-184, Medical Review
Taz gel and Taz gel vehicle - FDA Summary Basis of Approval for NDA 20-600, Medical Review As shown in Table 6, tretinoin that was formulated as a lotion according to the disclosure of Example 1 resulted in significantly fewer incidences of dry skin, erythema, desquamation, and burning/stinging as compared to ATRALIN® gel having the same amount of active agent. In contrast, formulating another retinoid, tazarotene, as a cream comprising mineral oil did not result in fewer incidences of dry skin, erythema, or desquamation as compared to the gel formulation of tazarotene.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, patent applications, or other documents cited herein are hereby incorporated by reference in their entirety for all purposes to the same extent as if each individual publication, patent, patent application, or other document was individually indicated to be incorporated by reference for all purposes.

What is claimed is:

1. A topical pharmaceutical composition for treating a skin condition or disorder, comprising:
   an active agent in an amount from 0.01% to 1% by weight of the composition, wherein the active agent consists of tretinoin;
   a polymeric emulsifier, wherein the polymeric emulsifier comprises a cross-linked copolymer of acrylic acid and C10-C30 alkyl acrylate, and wherein the polymeric emulsifier is present in an amount from 0.02% to 0.08% by weight of the composition;
   a viscosity increasing agent, wherein the viscosity increasing agent comprises a cross-linked homopolymer of an acrylic acid, and wherein the viscosity increasing agent is present in an amount from 0.1% to 2% by weight of the composition;
   a moisturizing agent, wherein the moisturizing agent comprises soluble collagen and sodium hyaluronate, and wherein the moisturizing agent is present in an amount from 5% to 10% by weight of the composition;
   an oil component comprising one or more oils, wherein the oil component is present in an amount from 1% to 3.5% by weight of the composition, and wherein each oil in the oil component is independently selected from the group consisting of mineral oil, light mineral oil, petrolatum, fatty alcohols, monocarboxylic acid esters, dicarboxylic acid esters, medium-chain triglycerides, and long-chain triglycerides; and
   water;
   wherein the composition is formulated as a lotion.

2. The topical pharmaceutical composition of claim 1, comprising the tretinoin in an amount of 0.05% by weight of the composition.

3. The topical pharmaceutical composition of claim 1, wherein the polymeric emulsifier is a carbomer copolymer type B.

4. The topical pharmaceutical composition of claim 1, wherein the oil component consists of mineral oil, light mineral oil, petrolatum, or a combination thereof.

5. The topical pharmaceutical composition of claim 1, wherein the oil component consists of mineral oil.

6. The topical pharmaceutical composition of claim 1, wherein the viscosity increasing agent is a carbomer homopolymer type A.

7. The topical pharmaceutical composition of claim 1, wherein the viscosity increasing agent is present in an amount from 0.1% to 2% by weight of the composition.

8. The topical pharmaceutical composition of claim 7, wherein the viscosity increasing agent is present in an amount from 0.6% to 1% by weight of the composition.

9. The topical pharmaceutical composition of claim 1, wherein the composition has a viscosity from 2,500 cP to 18,000 cP.

10. The topical pharmaceutical composition of claim 9, wherein the composition has a viscosity from 8,000 cP to 12,000 cP.

11. The topical pharmaceutical composition of claim 1, further comprising one or more preservatives, antioxidants, and/or humectants.

12. The topical pharmaceutical composition of claim 1, further comprising a neutralizing agent that maintains the pH of the composition at a pH from 5 to 6.

13. The topical pharmaceutical composition of claim 1, comprising:
   the tretinoin in an amount of 0.05% by weight of the composition;
   the polymeric emulsifier in an amount of 0.05% by weight of the composition, wherein the polymeric emulsifier is a carbomer copolymer type B;
   the viscosity increasing agent in an amount from 0.6% to 1% by weight of the composition; wherein the viscosity increasing agent is carbomer homopolymer type A;
   the oil component in an amount up to 3% by weight of the composition, wherein the oil component consists of mineral oil;
   the moisturizing agent in an amount from 5% to 10% by weight of the composition;
   a humectant in an amount from 5% to 20% by weight of the composition, wherein the humectant is glycerin;

an antioxidant in an amount from 0.1% to 2% by weight of the composition, wherein the antioxidant is butylated hydroxytoluene;

a wetting agent in an amount from 0.05% to 0.5% by weight of the composition, wherein the wetting agent is octoxynol-9;

optionally, one or more preservatives in an amount from 0.25% to 5% by weight of the composition, wherein the preservatives are benzyl alcohol, methyl paraben, or a combination thereof; and optionally, a neutralizing agent, wherein the neutralizing agent is trolamine.

14. The topical pharmaceutical composition of claim 1, wherein the composition has a viscosity of less than 15,000 cP.

15. The topical pharmaceutical composition of claim 14, wherein the composition has a viscosity from 8,000 cP to 12,000 cP.

16. A kit comprising the topical pharmaceutical composition of claim 1.

17. A method for treating a skin condition or disorder, comprising administering the topical pharmaceutical composition of claim 1 to a subject in need thereof.

18. The method of claim 17, wherein the skin condition or disorder is acne vulgaris.

19. The method of claim 17, wherein the topical pharmaceutical composition is applied once daily to an affected area of skin.

20. A topical pharmaceutical composition for treating a skin condition or disorder, wherein the topical pharmaceutical composition is formulated as a lotion and comprises:

an active agent an amount of 0.05% by weight of the composition wherein the active agent consists of tretinoin;

a carbomer copolymer type B in an amount from 0.04% to 0.06% by weight of the composition;

a carbomer homopolymer type A in an amount from 0.2% to 1% by weight of the composition;

soluble collagen and sodium hyaluronate in an amount from 5% to 10% by weight of the composition;

an oil component in an amount up to 3.5% by weight of the composition, wherein the oil component consists of mineral oil;

one or more preservatives, antioxidants, humectants, wetting agents, and/or neutralizing agents; and water.

21. A method for treating acne vulgaris, the method comprising applying to the skin of a subject having acne vulgaris the topical pharmaceutical composition of claim 20.

* * * * *